US00PP37086P2

(12) United States Plant Patent
Bergman

(10) Patent No.: US PP37,086 P2
(45) Date of Patent: Nov. 4, 2025

(54) ***CHRYSANTHEMUM* PLANT NAMED 'CIFZ0119'**

(50) Latin Name: ***Chrysanthemum* x *morifolium***
Varietal Denomination: CIFZ0119

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/055,613

(22) Filed: Feb. 18, 2025

(51) Int. Cl.
*A01H 6/14* (2018.01)
*A01H 5/02* (2018.01)

(52) U.S. Cl.
USPC ..... Plt./286

(58) Field of Classification Search
USPC ..... Plt./286
CPC ..... A01H 6/1424; A01H 5/02; A01H 6/14
See application file for complete search history.

*Primary Examiner* — Keith O. Robinson
(74) *Attorney, Agent, or Firm* — Dale Skalla

(57) ABSTRACT

A new *Chrysanthemum* plant named 'CIFZ0119' particularly distinguished by its dark pink and white striped flowers, daisy-type inflorescences, excellent flower production, moderate growth and spreading plant habit, and very uniform flowering with response time of 7 weeks when grown under short days.

1 Drawing Sheet

Latin name of the genus and species of the plant claimed: *Chrysanthemum* x *morifolium.*

Varietal denomination: 'CIFZ0119'.

BACKGROUND OF THE NEW PLANT

The present invention comprises a new *Chrysanthemum*, botanically known as *Chrysanthemum* x *morifolium*, and hereinafter referred to by the variety name 'CIFZ0119'.

'CIFZ0119' is a product of a planned breeding program. The new cultivar has dark pink and white striped flowers, daisy-type inflorescences, excellent flower production, moderate growth and spreading plant habit, and very uniform flowering with response time of 7 weeks when grown under short days.

'CIFZ0119' originates as a natural whole plant mutation discovered among flowering plants of 'CIDZ0100' growing in an outdoor field in Alva, Florida in July 2018. The parent 'CIDZ0100', U.S. Plant Pat. No. 33,369, sold commercially as 'Paisley Park Purple Bicolor', having inflorescences displaying a lower ratio of purple to white stripes under usual conditions, and a greater tendency to fade under hot growing conditions, while it is similar to 'CIFZ0119' in all other characteristics.

The first act of asexual reproduction of 'CIFZ0119' was accomplished when vegetative cuttings were propagated from the initial selection in October 2018 in a greenhouse in Gilroy, California.

BRIEF SUMMARY OF INVENTION

Horticultural examination of plants grown from cuttings of the plant initiated February 2019, and continuing thereafter, has demonstrated that the combination of characteristics as herein disclosed for 'CIFZ0119' are firmly fixed and are retained through successive generations of asexual reproduction.

'CIFZ0119' has not been observed under all possible environmental conditions. The phenotype may vary significantly with variations in environment such as temperature, light intensity and day length.

A Plant Breeder's Right for this cultivar has not yet been applied for. 'CIFZ0119' has not been made publicly available prior to the effective filing date of this application, notwithstanding any disclosure that may have been made less than one year prior to the effective filing date of this application by the inventor or another who obtained 'CIFZ0119' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings shows typical flower and foliage characteristics of 'CIFZ0119' with colors being as true as possible with an illustration of this type.

Figure 1:
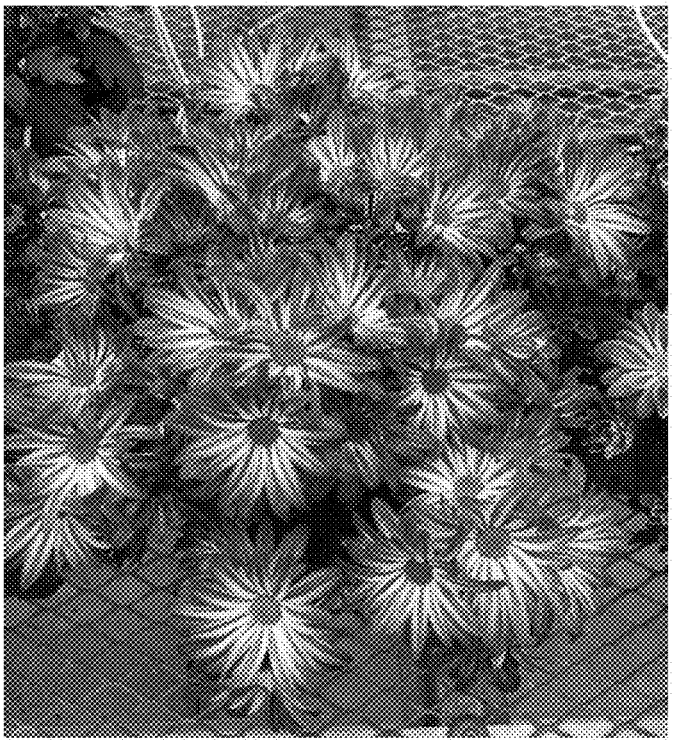

The whole plant photographic drawing, shown in FIG. 1, was taken in Gilroy, California in May 2024.

Figure 2:
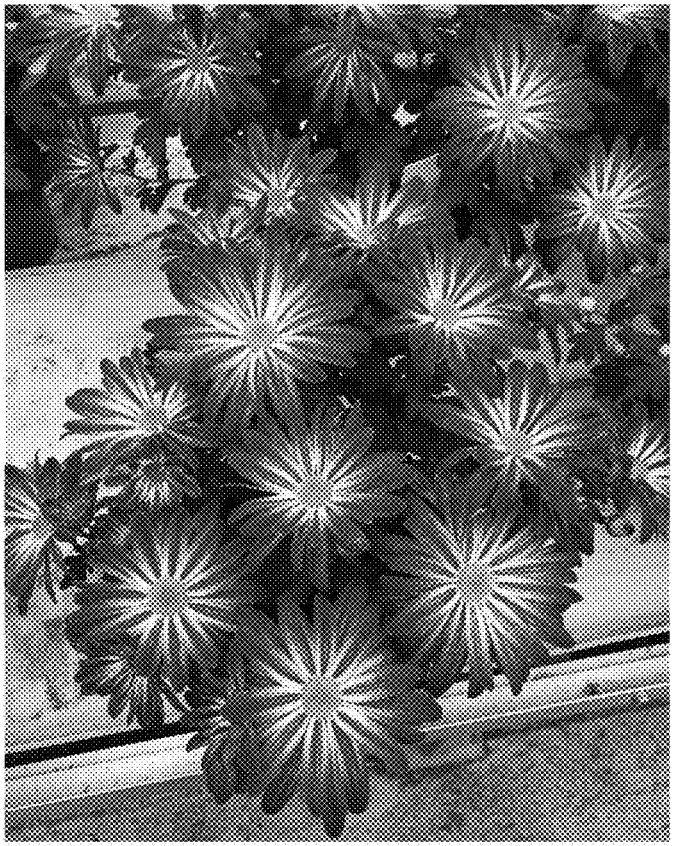

The close-up view of the inflorescense shown in FIG. 2, was taken in Milton, Ontario, Canada in February 2020 of plants approximately 12 weeks old.

DETAILED BOTANICAL DESCRIPTION

The plant descriptions and measurements were taken indoors in Gilroy, California in November 2024 on about 12 week old plants. Unrooted cuttings had been planted, 4 plants per pot, in 6 inch pots in August 2022. The plants were pinched and moved to short days in September 2022 to induce flowering.

Color references are made to The Royal Horticultural Society Colour Chart (RHS) 2001.

TABLE 1

DIFFERENCES BETWEEN THE NEW VARIETY 'CIFZ0119' AND A MOST SIMILAR VARIETY:

| | 'CIFZ0119' | 'Milton Pink Bicolor', unpatented |
|---|---|---|
| Plant height: | Shorter | Taller |
| Flower color: | Darker pink with white | Lighter pink with white |
| Flowering response: | Several days faster | Several days slower |
| Flower size: | Smaller | Larger |

Plant:

*Form, growth and habit.*—Herbaceous pot-type, stems upright, freely branching, strong and moderately vigorous growth habit.

*Plant height.*—17 cm.

*Plant height (inflorescence included).*—23 cm.

*Plant width.*—41 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—Closest to RHS N155B.

Foliage:

*Arrangement.*—Alternate.

*Immature, leaf color, upper surface.*—RHS 138A.

*Lower surface.*—RHS 138B.

*Mature, leaf color, upper surface.*—RHS 137A.

*Lower surface.*—RHS 137C.

*Length.*—5.3-5.8 cm.

*Width.*—4.2-4.5 cm.

*Shape.*—Ovate.

*Base shape.*—Attenuate.

*Apex shape.*—Mucronulate.

*Margin.*—Lobed with some serration.

*Texture, upper surface.*—Puberlulent.

*Lower surface.*—Puberlulent

*Color of veins, upper surface.*—RHS 138D.

*Color of veins, lower surface.*—RHS 138C.

*Pattern of veining.*—Pinnate.

*Petiole color.*—RHS 137A.

*Length.*—1.5-1.9 cm.

*Diameter.*—0.4-0.05 cm.

*Texture.*—Puberlulent.

Stem:

*Quantity of main branches per plant.*—3-4.

*Color of stem.*—RHS 138B.

*Length of stem.*—10-11 cm.

*Diameter.*—0.3-0.4 cm.

*Length of internodes.*—0.7-2.8 cm.

*Texture.*—Puberlulent.

*Color of peduncle.*—RHS 138B.

*Length of peduncle.*—4.0-7.2 cm.

*Peduncle diameter.*—0.2 cm.

*Texture.*—Puberlulent.

Inflorescence:

*Type.*—Compositae type, solitary daisy-type inflorescences borne terminally above foliage, ray florets arranged acropetally on a capitulum.

*Quantity of short days to flowering (response time).*—7 weeks.

*Natural season flowering.*—Not determined on this variety.

*Quantity of inflorescences per plant.*—9-12 flowers.

*Lastingness of individual blooms on the plant.*—4 weeks.

*Fragrance.*—Slightly spicy.

Bud (just when opening/showing color):

*Color.*—Closest to RHS 158C.

*Length.*—0.7-0.8 cm.

*Width.*—0.9-1.0 cm.

*Shape.*—Oblate.

Immature inflorescence:

*Diameter.*—6.2 cm.

*Color of ray florets, upper surface.*—RHS 5B.

*Lower surface.*—RHS 5C.

Mature inflorescence:

*Diameter.*—9.0-9.4 cm.

*Depth.*—2.4-2.9 cm.

*Total diameter of disc.*—1.6-1.7 cm.

*Receptacle color.*—RHS 145B.

*Receptacle height.*—0.4 cm.

*Receptacle diameter.*—0.6 cm.

Ray florets:

*Density of ray florets.*—Medium.

*Average quantity of florets.*—23.

*Color of ray florets, upper surface.*—Closest to RHS 72A and RHS 155D.

*Lower surface.*—Closest to RHS 155D and RHS 72B.

*Length.*—4.2-4.6 cm.

*Width.*—0.8-1.2 cm.

*Shape.*—Eliptical.

*Apex shape.*—Acute.

*Margin.*—Entire.

*Texture, upper surface.*—Smooth.

*Lower surface.*—Smooth.

Disc florets:

*Average quantity of florets.*—298.

*Color of florets.*—RHS 145B at the apex and RHS 154D at the base.

*Length.*—0.5-0.6 cm.

*Width.*—0.15 cm.

*Shape.*—Tubular, elongated.

*Apex shape.*—Acute, 5 pointed.

Phyllaries:

*Quantity.*—25-28.

*Color, upper surface.—RHS* 139A.

*Lower surface.*—RHS 137A.

*Length.*—0.7-0.9 cm.

Width.—0.25-0.4 cm.

*Shape.*—Lanceolate.

*Apex shape.*—Acute.

*Base.*—Fused.

*Margins.*—Entire; slightly papery.

*Texture, upper surface.*—Glabrous.

*Lower surface.*—Puberlulent.

Reproductive organs:

*Pistil.*—1, found on both types of florets.

*Length.*—0.6 cm.

*Style color.*—RHS 150C.

*Style length.*—0.5 cm.

*Stigma color.*—RHS 1C.

*Stigma shape.*—Bi-parted.

*Ovary color.*—RHS 155C but more translucent.

*Stamens.*—4, found only on the disc florets.

*Color of filaments.*—RHS 155C.

*Length filaments.*—0.4 cm.
*Anther color.*—RHS 1A.
*Anther length.*—0.1 cm.
*Anther shape.*—Oval.
*Color of pollen.*—Absent.
*Pollen amount.*—Absent.
*Fertility/seed set.*—Has not been observed to date.
*Disease/pest resistance.*—Has not been observed to date.

What is claimed is:

1. A new and distinct variety of *Chrysanthemum* plant named 'CIFZ0119' substantially as illustrated and described herein.

* * * * *